US00PP07795P

United States Patent [19]

Drewlow

[11] Patent Number: Plant 7,795

[45] Date of Patent: Feb. 18, 1992

[54] KALANCHOE PLANT NAMED REVELRY

[75] Inventor: Lyndon W. Drewlow, Ashtabula, Ohio

[73] Assignee: Mikkelsens, Inc., Ashtabula, Ohio

[21] Appl. No.: 607,378

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A new and distinct cultivar of Kalanchoe plant named Revelry, characterized by its deep, bright yellow flower color, early flowering, excellent keeping quality, good basal branching resulting in a dense, compact plant, dark green leaves, and floriferous habit which provides a full cover of flowers.

1 Drawing Sheet

The present invention relates to a new and distinctive cultivar of Kalanchoe plant, botanically known as Kalanchoe, and known by the cultivar name Revelry. Revelry was developed by me through controlled breeding by crossing Mikkelsen Seedling No. 84-2691-6 (seed parent) with Mikkelsen Seedling No. 84-2798-3 (pollen parent).

Asexual reproduction of stem cuttings has shown that the unique features of Revelry are stabilized and are reproduced true to type in successive propagations.

The following characteristics distinguish Revelry from both its parent varieties and other cultivated Kalanchoes of this type known and used in the floriculture industry, including the comparison cultivar Fortyniner, disclosed in U.S. Plant Pat. No. 5,256.

1. The flower color of Revelry is a deeper, brighter yellow (13A to 14A) while Fortyniner is a lighter, duller yellow (16A).

2. Flowering time for Revelry is 4 to 7 days earlier than Fortyniner under summer conditions and 10 to 14 days earlier under winter conditions from start of short day treatment.

3. Average flower diameter of Revelry is 13 to 14 mm while Fortyniner has an average diameter of 15 to 16 mm.

4. Average height of Revelry is 20 to 22 cm while Fortyniner is 23 to 25 cm high when grown under comparable conditions.

5. Keeping quality of individual flowers of Revelry is up to 7 days longer than Fortyniner; length of time plant remains in bloom after short day treatment is up to two weeks longer for Revelry compared to Fortyniner.

6. Fortyniner has larger leaves, averaging 6.0 to 6.5 cm wide and 10 cm long, while Revelry has leaves 5.5 to 6.0 cm wide and 7.5 to 8.5 cm long.

7. Revelry and Fortyniner have similar dark green leaves and the venation is similar. However, Fortyniner has more anthocyanin pigmentation at the leaf margin and a more cupped leaf than Revelry.

8. Peduncle of main stem of Fortyniner just below first major branch in the inflorescence is 8 mm in diameter, compared to 4 mm for Revelry.

9. Revelry is more heavily basal branched than Fortyniner which results in a denser, more compact habit of growth.

10. Compared to Fortyniner, Revelry has many more flowers in the inflorescence. The shorter pedicels of Revelry result in a full cover of flowers over the plant. Fortyniner is a more open growing plant in which the inflorescence does not present itself as a solid mass of flowers since there are openings in the inflorescence.

The accompanying colored photograph illustrates in front perspective view the overall appearance of Revelry showing the colors as true as it is reasonably possible to obtain in a colored reproduction of this type. The photograph was taken on Mar. 23, 1990 under natural light on an overcast day under double poly greenhouse covering at Ashtabula, Ohio.

The following is a detailed description of my new cultivar, based on plants produced in greenhouses in Ashtabula, Ohio during the late spring to summer season of the year. Plants were grown in 10 cm pots and measurements were taken 12 weeks after rooted cuttings were planted. Height measurements were taken from the soil line of the container. The plants were grown at 65°-68° F. night temperatures, under 3500-4000 foot candles of light, and 240 ppm nitrogen, 240 ppm potassium, and 175 ppm phosphorous nutritional levels with trace elements added. 5000 ppm B-9 was applied week three and week 5 of short day treatment of the six week short day treatment (14 hours dark) period.

Colors references are made to the Royal Horticultural Society Colour Chart except where general terms of ordinary dictionary significance are used.

Parentage: A controlled cross between female Mikkelsen Seedling No. 84-2691 and male Mikkelsen Seedling No. 84-2798-3.

Propagation:

(A) *Type cutting.*—Stem tip cutting up to 3 cm long.

(B) *Time to root.*—10 days at 21° C. in summer; 14 days at 21° C. in winter.

(C) *Rooting habit.*—Fine, abundant, fibrous roots.

Plant description:

(A) *Habit and form of growth.*—Compact, excellent basal branching resulting in a semi-upright growth habit; flower clusters held well above foliage; environment and use of growth regulators will play a role in final height.

(B) *Foliage description.*—Leaves simple and opposite. 1. Size: Average; full grown leaves on a plant when grown in a 10 cm pot are 7.5 to 8.5 cm long by 5.5 to 6.0 cm wide. 2. Shape: Ovate, apex obtuse to acute; base rounded. 3. Texture: Glabrous, coriaceous, and succulent. 4. Margin:

Crenate; moderately lobed. 5. Color: Young foliage, top side 144B; under side 146C. Mature foliage, top side between 147A and 147B; underside between 147B and 147C.

Flowering description:

(A) *Flowering habit.*—Inflorescence is a cyme. Terminal flower on main axis opens first, followed by the terminal flowers of the side branches, continuing with the subsequent development of branches in the inflorescence. Inflorescence is made up of the main stem and up to 10 or more lateral branches. Lower lateral branches are last to develop.

(B) *Natural flowering season.*—Early January. Flowering time under controlled daylength at 20° C. in summer is 10½ weeks; in winter is 12 weeks. Flowering time depends on temperature, light intensity and other growing conditions.

(C) *Flower buds.*—Oblong, up to 5 mm long before showing color, developing tubular as flower petals mature; sheathed in four light green sepals.

(D) *Flowers borne.*—On compound dichasial cymes, primary peduncle 4 mm in diameter just below the first branch of the inflorescence; length will vary depending on growing conditions. Pedicels vary in length depending on where they are located in the inflorescence.

(E) *Quantity of flowers.*—Very floriferous as main stem plus 10 or more laterals and each having 35 to 50 or more flowers.

(F) *Petals.*—1. Shape: Almost rounded; top cuspidate. 2. Color: Top side when opening 13A to 14A, fading to 14C; under side 14D. 3. Number of petals: Four. 4. Size: Individual petals 6 mm wide and 7 mm long; flower 14 mm in diameter.

Reproductive organs:

1. *Stamens.*—Eight in number. a. Anther shape: Flat, elliptical, color yellow-green. b. Filament color: Yellow-green. c. Pollen color: Yellow.
2. *Pistils.*—a. Stigma shape: Flat; color whitish (mature). b. Style color: Light green. c. Ovaries: Four in number; size 5 mm; color green.

Disease resistance: Revelry has shown resistance to Powdery Mildew and no disease problems have been noted to date.

Other important characteristics: Revelry is part of a series of Kalanchoes that include Majestic, Splendor, Keepsake and Heirloom (all disclosed in pending plant patent applications of applicant) that are similar in flowering time, height, branching and response to growth regulators. This allows greenhouse growers to handle five distinctly different colors at the same time from a single planting date and use the same growing methods on each to end up with a uniform crop. The end results are easier crops for the growers to produce and higher quality crops. All cultivars are ideal for both 10 and 15 cm pot production.

I claim:

1. A new and distinct cultivar of Kalanchoe plant named Revelry, as illustrated and described.

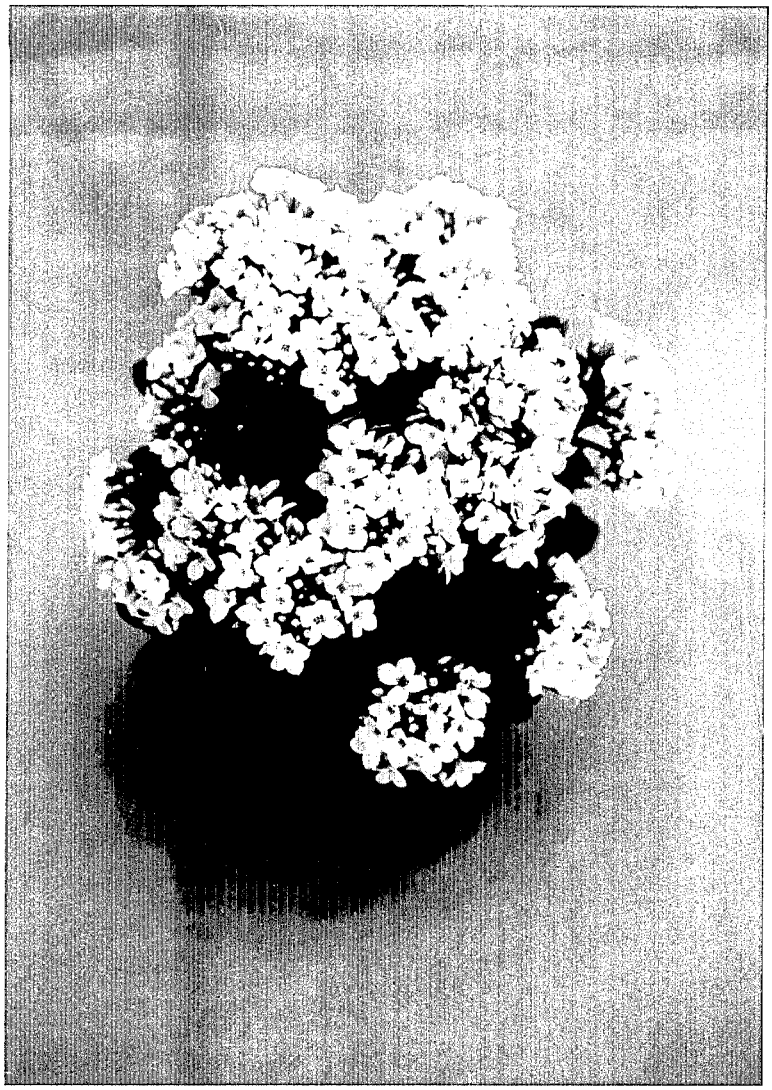

* * * * *